United States Patent [19]

Erlich et al.

[11] Patent Number: 5,409,484
[45] Date of Patent: Apr. 25, 1995

[54] CAUTERY WITH SMOKE REMOVAL APPARATUS

[76] Inventors: Frederick Erlich, 29540 Meadowland Dr., Southfield, Mich. 48076; Ted Schartzenfeld, 4855 Rolling Ridge, W. Bloomfield, Mich. 48232

[21] Appl. No.: 607,107
[22] Filed: Sep. 24, 1990
[51] Int. Cl.6 .............................................. A61M 1/00
[52] U.S. Cl. ........................................ 606/34; 606/41; 604/27; 128/897
[58] Field of Search .................... 128/897; 604/20–22, 604/27, 35; 606/27–29, 34, 37–42, 45, 49

[56] References Cited

U.S. PATENT DOCUMENTS

| | | | |
|---|---|---|---|
| 2,275,167 | 3/1942 | Bierman | 606/49 |
| 3,906,955 | 9/1975 | Roberts | 604/21 |
| 4,307,720 | 12/1981 | Weber, Jr. | 604/22 |
| 4,715,372 | 12/1987 | Philppba et al. | 606/10 |

*Primary Examiner*—David M. Shay
*Attorney, Agent, or Firm*—Reising, Ethington, Barnard, Perry & Milton

[57] ABSTRACT

A cautery, for performing surgical operations through the application of heat to soft tissue, is provided with a smoke removal apparatus to remove smoke and vapors from the immediate area of an operation during use. In a preferred embodiment, the smoke removal apparatus includes a tube disposed proximate to a cutting tip of the cautery, the tube being connected at an opposite end thereof to a vacuum source.

4 Claims, 1 Drawing Sheet

CAUTERY WITH SMOKE REMOVAL APPARATUS

BACKGROUND OF THE INVENTION

1. Field of the Invention

The present invention relates to a cautery, which is a device for surgically cutting tissue through the application of heat thereto. More particularly, the present invention relates to a cautery which includes an apparatus for removal of smoke and other combustion products from the immediate vicinity of the cutting tip thereof.

2. Prior Art

The basic design of a cautery apparatus, per se, is known in the art and is commonly used in the medical arts for performing operations on soft tissue such as, e.g., performing tonsillectomies and the like. However, the known prior art cauteries suffer from a drawback, in that in use thereof, considerable amounts of smoke are generated by the cauterizing process, and this smoke tends to interfere with the visibility to the doctor of the area being operated on.

A number of prior art patents on surgical devices are discussed below.

L'Esperance, U.S. Pat. No. 3,982,541 discloses an apparatus for removing surface portions of an eye such as cataract tissue. The cataract tissue or other portions to be removed are vaporized by a carbon dioxide laser beam. The apparatus of L'Esperance includes a probe having a central tube open at both ends. One end of the central tube is disposed within the probe, while the other end of the tube projects from the probe. A beam of collimated light is projected through the central tube to the portion of the eye to be removed. Smoke and vaporized portions of tissue are removed through the central tube by the use of a vacuum pump connected to the device.

Lu et al, U.S. Pat. No. 4,796,622 discloses a thermal-tipped double catheter for use in thermal angioplasty to remove obstructions from arteries. The apparatus of Lu utilizes heat, generated by the reaction of oxygen and hydrogen gasses, catalyzed by a small piece of palladium sponge situated in a chamber adjacent to and enclosed by the metallic tip of the catheter. Vapors which are formed in the chamber of the catheter are removed by a vacuum applied to an inner tube thereof.

Although certain surgical devices which incorporate smoke removal means are known, it would be advantageous if a cautery could be adapted for use with a smoke removal apparatus because of the smoke generated in the use thereof.

SUMMARY OF THE INVENTION

The present invention provides a cautery which incorporates a smoke removal device thereon. The smoke removal apparatus hereof may include a vacuum pump.

A cautery in accordance with the present invention, generally, comprises:

(a) a handle;
(b) a cord extending outwardly from the handle and having wires therein which are connectable to an electrical power source;
(c) a cutting tip extending outwardly from one end of the handle;
(d) a tube disposed proximate the cutting tip to remove smoke and vapors therethrough when connected to a vacuum source; and
(e) a vacuum source in communication with the tube to pull smoke and vapors therethrough.

For a more complete understanding of the present invention, reference is made to the following detailed description section, which should be read in conjunction with the accompanying drawings. Throughout the following description and in the claims, like reference numbers refer to like parts throughout the drawings, in which:

DETAILED DESCRIPTION OF THE PREFERRED EMBODIMENT

Figures 1, 2:
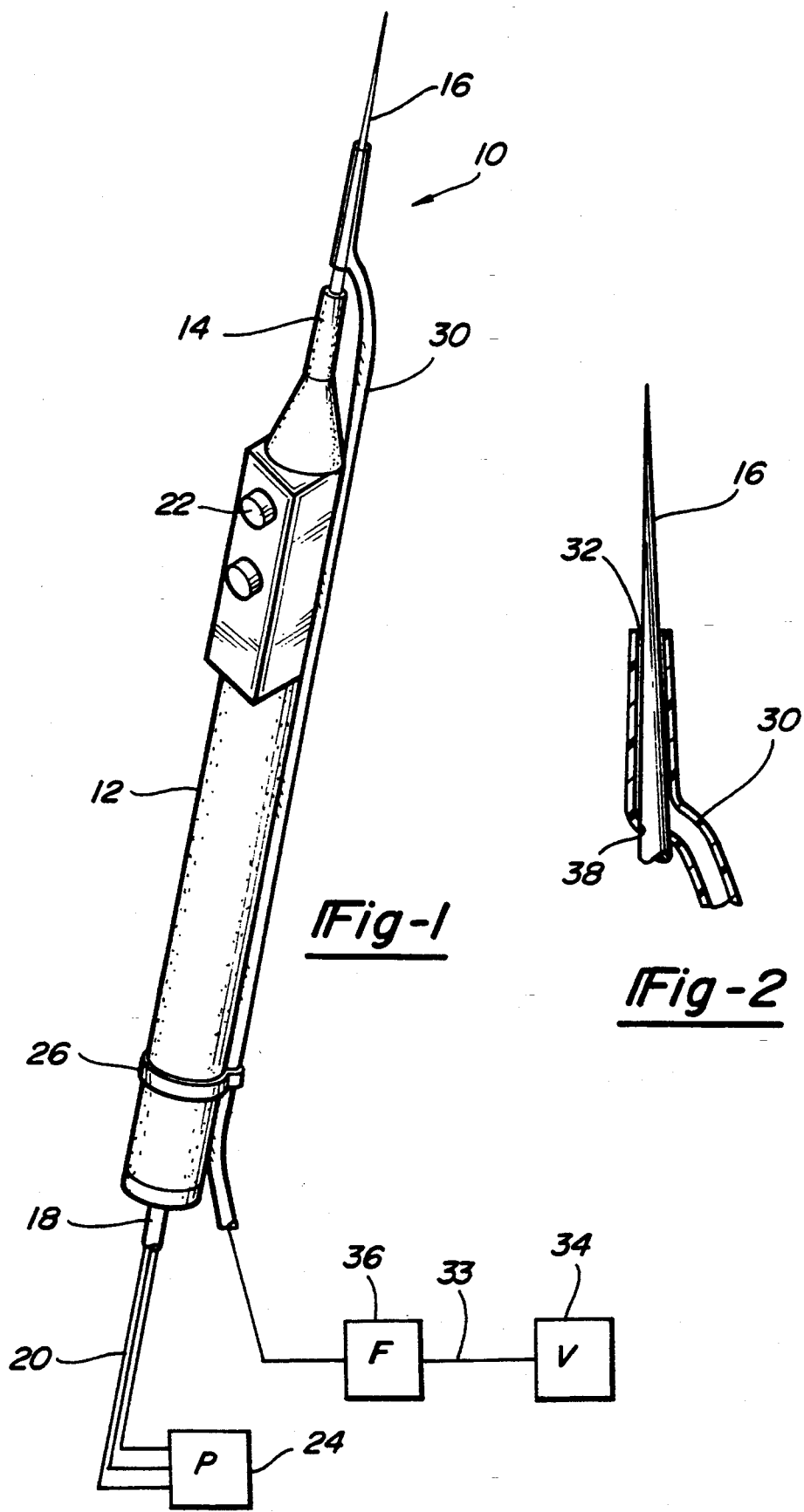
FIG. 1 is a perspective view, partially schematic, of a cautery in accordance with the present invention.
FIG. 2 is a cross-sectional view of the cautery tip of the device of FIG. 1.

Referring to the drawings, a cautery in accordance with the present invention is, generally shown at 10. The cautery 10 includes a handle 12, which is a generally tubular body, which is tapered at an upper end 14 thereof to a narrowed diameter. A cutting tip 16, which is generally needle-shaped and tapers to a point, extends outwardly from the upper end 14 of the handle 12. The cutting tip 16 is, generally, formed of metal and comprises an electrical resistor which enables the tip 16 to become extremely hot when the cautery 10 is connected to an electrical power source 24.

A cord 18 extends outwardly from the handle 12 at the lower end thereof, and the cord 18 contains a plurality of wires 20 therein for communicating with the electrical power source 24. One or more buttons 22 are provided on the handle 12 for putting the cutting tip 16 into electrical communication with the wires 20 to cause the cutting tip 16 to become hot. The button 22 activates an electrical switch (not shown) within the handle 12 to place the cutting tip 16 into and out of electrical communication with the power source 24 through the wires 20. The button 20 is similar to those found in conventional cautery designs.

A flexible tube 30 is disposed next to the handle 12 and terminates at an opening 32 proximate the cutting tip 16. The tube is preferably attached to the handle 12 by any suitable means, such as, e.g., the band clamp 26 shown in the drawings. The tube 30 is preferably formed from a resilient heat-resistant material. Heat-resistant plastic may be used. The tube 30 is connected at an end 33 thereof opposite the handle 12, to a vacuum source 34, such as an electrical vacuum pump or the like. A filter 36, having a removable cartridge (not shown) therein, may optionally be placed in line with the tube 30 between the handle 12 and the vacuum source 34 to filter materials out of the tube 30 and to protect the vacuum source 34. The tube 30, in the embodiment shown, is pierced by the cutting tip 16 to form an aperture 38 therein, arid the tube 30 completely surrounds the cutting tip 16 for part of its length where the tube 30 extends upwardly above the aperture 38, as shown in the drawings. By the use of the tube 30, in combination with the vacuum source 34, a low pressure area can be created at the opening 32 and in the area adjacent the exposed section of the cutting tip 16, in order to draw smoke and vapors away from the immediate area of the cutting tip 16 in use. This services the dual function of allowing improved visibility to a doctor who is performing an operation using the cautery 10 while at the same time removing troublesome smoke which could potentially interfere with the breathing of the patient (not shown) during the course of an operation.

Although the present invention has been described with reference to a specific embodiment thereof, it will be understood that the foregoing description is intended to be illustrative and not restrictive. Many modifications of the present invention will occur to those skilled in the art. All such modifications which fall within the scope of the appended claims are intended to be within the scope and spirit of the present invention.

Having, thus, described the invention, what is claimed is:

1. A cautery for operating on soft tissues by applying heat thereto, comprising:
   (a) a handle;
   (b) a cord extending outwardly from the handle and having wires therein which are connectable to an electrical power source;
   (c) a cutting tip extending outwardly from one end of the handle;
   (d) a tube being operatively attached to the handle, the tube having an open end which is disposed surrounding a portion of the cutting tip for removing smoke and vapors therethrough, the tube being connectable to a vacuum source for pulling smoke and vapors therethrough;
   (e) the tube being formed from a resilient heat-resistant material.

2. The cautery of claim 1, further comprising a filter disposed in fluid communication with the tube for filtering material which passes through the tube.

3. The cautery of claim 1, further comprising means for putting the cutting tip into electrical communication with the wires to cause the cutting tip to become hot.

4. The cautery of claim 1, wherein the tube is pierced by the cutting tip to form an aperture therein.

* * * * *